United States Patent [19]
Vasella et al.

[11] Patent Number: 6,143,725

[45] Date of Patent: Nov. 7, 2000

[54] GLYCOSYLATED GINKGOLIDE DERIVATIVES, THEIR APPLICATION AS MEDICINES AND PHARMACEUTICAL COMPOSITIONS

[75] Inventors: Andrea Vasella, Zurich; Martin Weber, Paradiso, both of Switzerland

[73] Assignee: Societe de Conseils de Recherches et d'Applications Scientifiques (S.C.R.A.S), France

[21] Appl. No.: 09/424,207

[22] PCT Filed: May 20, 1998

[86] PCT No.: PCT/FR98/01016

§ 371 Date: Nov. 30, 1999

§ 102(e) Date: Nov. 30, 1999

[87] PCT Pub. No.: WO98/52959

PCT Pub. Date: Nov. 26, 1998

[30] Foreign Application Priority Data

May 20, 1997 [FR] France ................... 97 06111

[51] Int. Cl.⁷ ............... A61K 31/70; C07G 3/00

[52] U.S. Cl. .............................. 514/27; 536/18.5

[58] Field of Search ............... 514/27; 536/18.5

[56] References Cited

U.S. PATENT DOCUMENTS

| | | | |
|---|---|---|---|
| 4,734,280 | 3/1988 | Braquet | 424/195.1 |
| 5,002,965 | 3/1991 | Ramwell et al. | 514/468 |
| 6,030,621 | 2/2000 | Long et al. | 424/195.1 |

FOREIGN PATENT DOCUMENTS

| | | | |
|---|---|---|---|
| 2622448 | 11/1988 | France | 424/195.1 |
| 3514054 | 1/1986 | Germany | 514/58 |

*Primary Examiner*—James H. Reamer
*Attorney, Agent, or Firm*—Bierman, Muserlian and Lucas

[57] ABSTRACT

The invention relates to new glycosylated derivatives of ginkgolides, their use as medicaments and the pharmaceutical compositions containing them.

The invention also provides a preparation process for these derivatives.

8 Claims, No Drawings

GLYCOSYLATED GINKGOLIDE DERIVATIVES, THEIR APPLICATION AS MEDICINES AND PHARMACEUTICAL COMPOSITIONS

This application is a 371 of PCT/FR98/01016 filed May 20, 1998.

The present invention relates to new glycosylated derivatives of ginkgolides, as well as their use as medicaments. Such derivatives can in particular be used in pharmaceutical compositions.

The properties of ginkgolides (anti-PAF ("Platelet Activating Factor") activity, inhibition of the formation of free radicals, inhibition of the release of glucocorticoids, etc.) are known (cf. in particular Patent Applications DE-A 35 14 054, EP 0 431 535; Amri, Ogwuegbu, Boujrad, Drieu, Papadopoulos, *Endocrinology*, 137(12), 5707–5718). However, their pharmaceutical activity is limited by their low solubility in water. The Applicant has noted that the glycosylation of these ginkgolides leads to new hydrosoluble products, therefore more easily usable for pharmaceutical compositions whilst preserving the initial biological activity of the ginkgolides or even improving it.

The invention relates in particular to mono-, di-, or, if appropriate tri- or tetraglycosylated derivatives of ginkgolides A, B, C, J or M (structures given in the diagram below; these compounds can be isolated from leaf extracts of *Ginkgo biloba*—see GINKGOLIDES, Chemistry, Biology, Pharmacology and Clinical Perspectives, edited by P. Braquet, J. R. Prous Science Publishers, in particular Volumes 1 (1988) and 2 (1989)). It also relates to glycosylated derivatives of alkoxylated derivatives of ginkgolides, i.e. those comprising at least one linear or branched alkoxy group, instead of a hydroxy group (these compounds are described in the French Patent Application FR 88.14392).

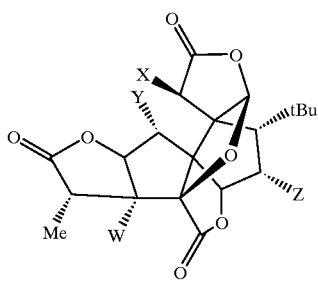

| Ginkgolide | W | X | Y | Z |
|---|---|---|---|---|
| A | OH | OH | H | H |
| B | OH | OH | OH | H |
| C | OH | OH | OH | OH |
| J | OH | OH | H | OH |
| M | H | OH | OH | OH |

Structure of ginkgolides A, B C, J and M

The invention relates to a compound of the general formula (I)

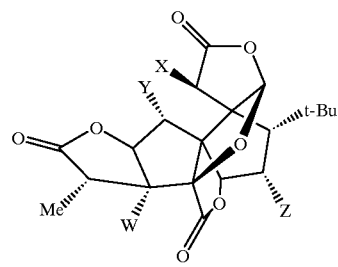

in which W, X, Y and Z represent independently H, OH, linear or branched alkoxy radicals, or O—$G_s$, $G_s$—OH representing a mono- or a disaccharide, or one of their derivatives or analogues, it being understood that at least one of W, X, Y or Z represents an O—$G_s$ radical.

The invention preferably relates to a compound of general formula (I)

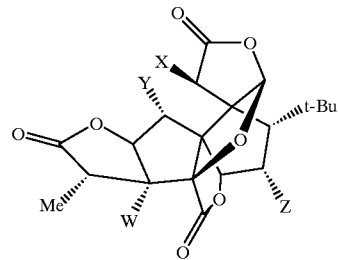

in which X represents an OH or O—$G_s$ radical, $G_s$—OH representing a mono- or a disaccharide, or one of their derivatives or analogues, and:

either W represents a OH or O—$G_s$ radical, Y represents H and Z represents H;

or W represents an OH or O—$G_s$ radical, Y represents an OH or O—$G_s$ radical and Z represents H;

or W represents an OH or O—$G_s$ radical, Y represents an OH or O—$G_s$ radical and Z represents an OH or O—$G_s$ radical;

or W represents an OH or O—$G_s$ radical, Y represents H and Z represents an OH or O—$G_s$ radical;

or W represents H, Y represents an OH or O—Gs radical and Z represents an OH or O—Gs radical;

or W represents an OH or O—Gs radical, Y represents a linear or branched alkoxy radical and Z represents H;

it being understood that at least one of W, X, Y or Z represents an O—$G_s$ radical.

The invention relates more particularly to a compound of the general formula (I)

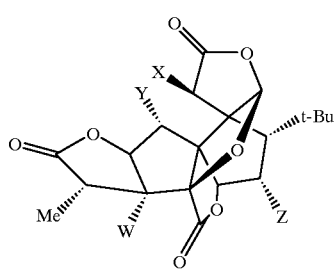

(I)

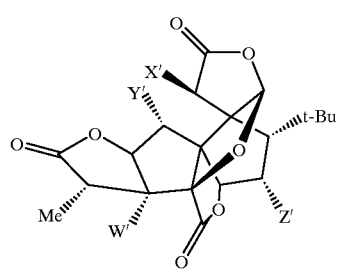

(III)

in which X represents an OH or O—Gs radical, $G_s$—OH representing a mono- or a disaccharide, or one of their derivatives or analogues, and:

either W represents an OH or O—Gs radical, Y represents H and Z represents H;

or W represents an OH or O—Gs radical, Y represents an OH or O—Gs radical and Z represents H;

or W represents an OH or O—Gs radical, Y represents a linear or branched alkoxy radical and Z represents H; it being understood that at least one of W, X, Y or Z represents an O—Gs radical.

By linear or branched alkoxy radical is understood in the present description an alkoxy radical, the carbonated chain of which, linear or branched, has 1 to 6 carbon atoms. By mono- or disaccharide derivative or analogue is meant compounds such as N-acetylglucosamine, the N-acetylalosamine, galactosamine, mannoseamine, N-tosylhydrazone, etc.

Preferably, O—$G_s$ will be chosen such that $G_s$—OH forms part of the group composed of abequose, rhamnose, arabinose, ribose, xylose, 2-deoxyribose, glucose, galactose, mannose, 2-deoxyglucose, fructose, fucose, N-acetylglucosamine, N-acetylalosamine, galactosamine, mannosamine, saccharose, lactose, maltose, cellobiose and trehalose. In a yet more preferable manner, O—$G_s$ will be chosen such that $G_s$—OH forms part of the group composed of glucose and lactose.

The invention therefore relates in particular to glycosylated derivatives of ginkgolides, more particularly those of ginkgolides A and B, the glycosyl groups suitable for the invention being described previously.

The invention also provides a process for obtaining glycosylated derivatives of ginkgolides or of alkoxylated ginkgolides (i.e. those resulting from a glycosylation reaction carried out on at least one of the OH groups of ginkgolides or their alkoxylated derivatives). This process mainly comprises a glycosylation stage which consists of a reaction of a compound of general formula (III) represented below, in which W', X', Y' and Z' represent independently a H, OH, linear or branched alkoxy or O—$G_x$ radical, $G_x$ being a protective group of a hydroxy group preferably being able to be eliminated in a neutral or basic medium, it being understood that at least one of W', X', Y' and Z' represents OH, with a glycosyl diazirine of general formula (II) represented below, the reaction preferably taking place in THF at temperatures preferably comprised between 20 and 60° C.

(II)

Compound (II) is a diazirine derivative of a $G_p$—OH sugar, all the hydroxy groups of which, except that carried by the anomeric carbon have been protected, for example by benzyl or silyl radicals, whilst the hydroxy group in anomeric position and the hydrogen carried by the same carbon atom have been substituted by an azi group.

Said process can also include one or more protection and/or deprotection stages of the hydroxy groups. For these stages, a person skilled in the art uses the standard methods available (Greene, T., Protective Groups in Organic Synthesis 10–86 (John Wiley & Sons 1981)) and he preferably chooses protective groups which can be eliminated in a basic or neutral medium.

The glycosylation reaction will generally produce, in the case where an excess of glycosyldiazirine is used, a mixture of mono- and diglycosylated derivatives for gingkolide A or a mixture of mono-, di- and triglycosylated derivatives for ginkgolide B.

In all cases where a mixture of products is obtained, a separation of these products according to the methods known to a person skilled in the art is carried out (in particular, filtration on silica or high-performance liquid chromatography with a suitable eluant, or also crystallization or recrystallization from an appropriate solvent).

The sugars or sugar derivatives which can be used for the glycosylation of ginkgolides can be in particular abequose, rhamnose, arabinose, ribose, xylose, 2-deoxyribose, glucose, galactose, mannose, 2-deoxyglucose, fructose, fucose, saccharose, lactose, maltose, cellobiose, trehalose, N-acetylglucosamine, N-acetylallosamine, galactosamine, mannosamine, derivatives of these compounds, in particular corresponding diazirines, or also N-arylsulphonyl hydrazones such as N-tosylhydrazone and their salts.

When the method used is the addition of glycosyl diazirine (general method described in Briner, K., Vasella, A., Helv. Chim. Acta, 72, 1371 (1989)), in particular the following diazirines can be used:

- 1-azi-2,3,4,6-tetra-O-benzyl-1-deoxy-D-glucopyranose or 1-azi-1-deoxy-2,3:5,6-di-O-isopropylidene-D-mannofurannose (syntheses described in Briner, K., Vasella, A., Helv. Chim. Acta, 75(2), 621–637 (1992));
- 1-azi-2,3,4,6-tetra-O-benzyl-1-deoxy-D-galactopyranose (synthesis described in Briner, K., Vasella, A., Helv. Chim. Acta, 73(6), 1764–1779 (1990));
- 1-azi-2,3,4,6-tetra-O-benzyl-l-deoxy-D-mannopyranose (synthesis described in Vasella, A., Witzig, C., Waldraff, C., Uhlmann, P., Briner, K., et al., Helv. Chim. Acta, 76(8), 2847–2875 (1993));
- 2-acetamido- 1,5-anhydro- 1-azi-3-O-benzyl-4,6-O-benzylidene- 1,2-dideoxy-D-allitol (synthesis described in Vasella, A., Dhar, P., Witzig, C., Hetv. Chim. Acta, 76(4), 1767–1778 (1993) and Linden, A., Vasella, A., Witzig, C., Helv. Chim. Acta, 75(5), 1572–1577 (1992));
- 1,5-anhydro-1-azi-2-deoxy-3.4,6-tri-0-pivaloyl-D-glucitol (synthesis described in Takahashi, Y., Vasella, A., Helv. Chim. Acta, 75(5), 1563–1571 (1992));
- 1,5-anhydro-1-azi-2.3,4,6-tetra-O-pivaloyl-D-glucitol or 2-acetamnido-1,5-anhydro-1-azi-3-O-benzyl-4,6-O-benzylidene-1,2-dideoxy-D-glucitol (syntheses described in Vasella, A., Witzig, C., Waldraff, C., Uhlmann, P., Briner, K., et al., Helv. Chim. Acta, 76(8), 2847–2875 (1993));
- 1,5-anhydro-1-azi-2,3-di-O-benzyl-4,6-O-benzylidene-D-mannitol (synthesis described in Uhlmann, P., Briner, K., et al., Helv. Chim. Acta, 76(8), 2847–2875 (1993));
- 1,5-anhydro-1-azi-2,3-di-O-benzyl-4,6-O-(4-methoxybenzylidene)-D-glucitol (synthesis described in Vasella, A., Witzig, C., Waldraff, C., Uhlmann, P., Briner, K., et al., Helv. Chim. Acta, 76(8), 2847–2875 (1993));
- 2-acetamido-1,5-anhydro-1-azi-3,4,6-tri-O-benzyl-2-deoxy-D-glucitol (synthesis described in Vasella, A., Witzig, C., Waldraff, C., Uhlmann, P., Briner, K., et al., Helv. Chim. Acta, 76(8), 2847–2875 (1993));
- 1-azi-1-deoxy-2,3:4,6-di-O-isopropylidene-D-glucopyranose (synthesis described in Uhlmann, P., Harth, E., Naughton, A. B., Vasella, A., Helv. Chim. Acta, 77(8), 2335–2340 (1994));
- (Z)-N'-2,3,5-tri-O-benzyl-D-(ribofuranosylidene)toluene-4-sulphonohydrazide or (Z)-N'-2,3,5-tri-O-benzyl-D-(arabinofuranosylidene)toluene-4-sulphonohydrazide (synthesis described in Mangholz, S. E., Vasella, A., Helv. Chim. Acta, 78(4), 1020–1035 (1995));
- 1-azi-2,3,6-tri-O-benzyl-4-O-[2,3,4,6-tetra-O-benzyl-D-galactopyranosyl]1-deoxy-D-glucopyranose (synthesis according to Briner, K., Vasella, A., Helv. Chim. Acta, 72, 1371 (1989)).

A person skilled in the art can of course choose other compounds of the same type if deemed necessary.

The solvents which can be used for the glycosylation reaction are 1,4-dioxane, THF, toluene, methylene chloride or 1,2-dichloroethane. Preferably, THF is used.

The reaction conditions can be thermal or photolytic conditions. As regards thermal conditions, the operation is carried out at temperatures preferably comprised between 25 and 60° C. As regards photolytic conditions, the operation is carried out at low temperature, typically between –80° C. and –60° C., generally with THF as solvent. As regards the photolysis, a Philips HPK-125 high-pressure mercury lamp can preferably be used. Typically, irradiation will be carried out for a period of approximately one hour, or longer if necessary.

For the monoglucosylated derivatives of ginkgolide A, a possible synthesis route is the following:

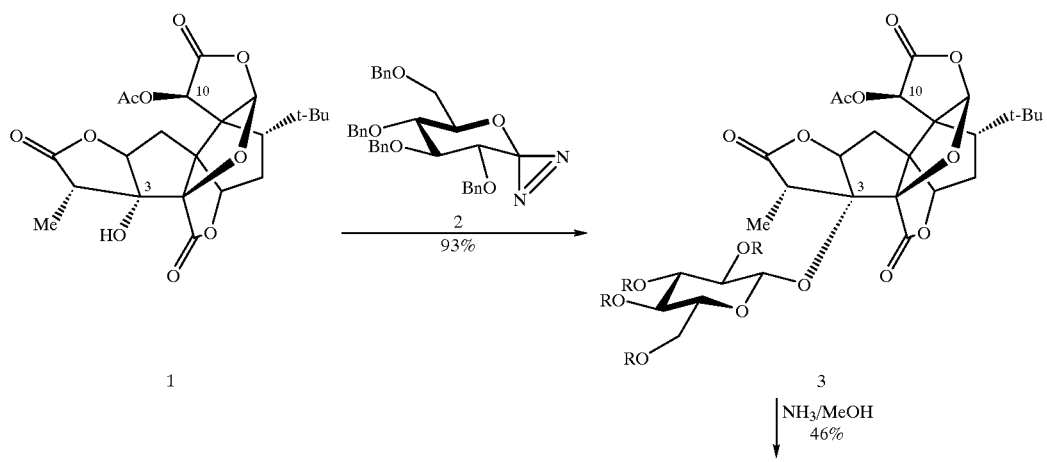

-continued

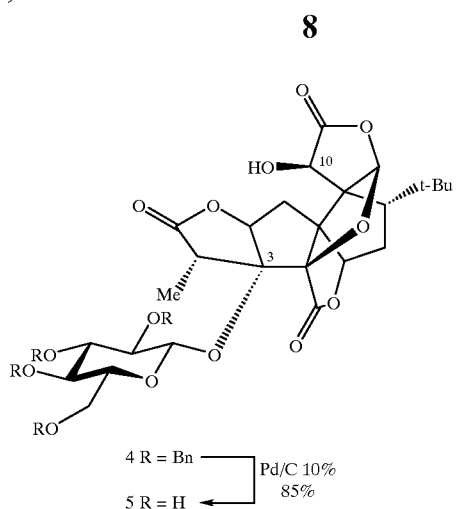

4 R = Bn  ⎤ Pd/C 10%
5 R = H  ⎦ 85%

The 10-O-acetyl-ginkgolide A (1) (prepared from ginkgolide A which is reacted for 25 hours at ambient temperature with excess acetic anhydride in pyridine) is treated for one hour and 30 minutes at 30° C. with approximately 1.3 equivalent of glucosyl diazirine 2, the reaction being carried out in THF. After evaporation and crystallization, 3 is then obtained which is treated with $NH_3$ in MeOH in order to produce the deacetylated product 4. The debenzylation of 4 is then carried out in a standard manner by hydrogenation with 10% Pd/C in MeOH. 3-O-(β-D-glucopyranosyl)ginkgolide A (5) is then obtained. It should be noted that the debenzylation and deacetylation stages can be interchanged.

In the same way as the synthesis of the monoglucosylated derivatives of ginkgolide A is carried out, that of the monoglycosylated derivatives of ginkgolide A can be carried out using glycosyl diazirines other than those described previously or by carrying out the glycosylation reaction under standard conditions (described in the literature).

By way of example, 3-O-[(4-O-β-D-galactopyranosyl)-β-D-glucopyranosyl]ginkgolide A can be obtained using the following route:

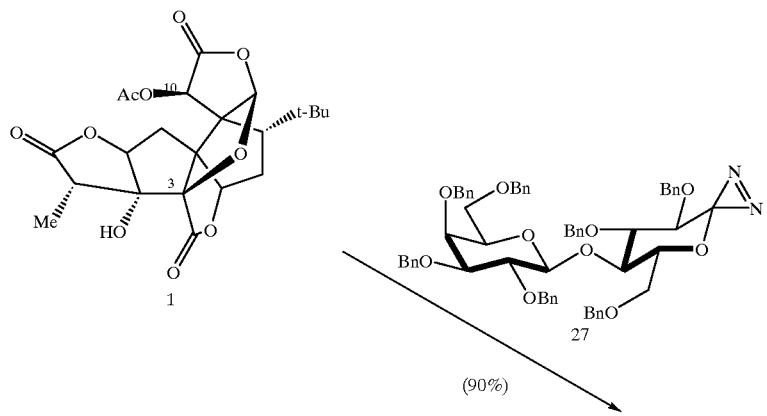

-continued

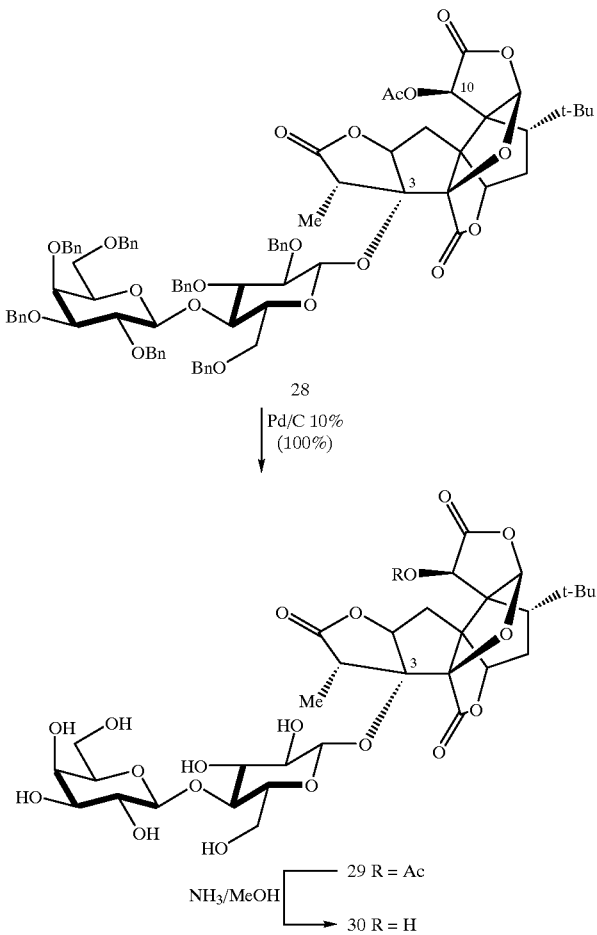

The ginkgolide A (1) is treated with a solution of diazirine 27 in THF for one hour. 28 is then obtained with a yield of 90%. 28 is debenzylated by hydrogenation in the presence of 10% Pd/C to produce 29. Finally, 29 can be deacetylated using standard methods (for example NH$_3$/MeOH) to produce 3-O-[(4-O-β-D-galactopyranosyl)-β-D-glucopyranosyl]ginkgolide A (30). Naturally, the two last stages can be interchanged as previously.

If the diglycosylated derivative of ginkgolide A is desired to be obtained, it is sufficient to start with ginkgolide A and not 10-O-acetyl-ginkgolide A (1), and to use an excess of glycosyldiazirine or glycosylating reagent if another glycosylation reaction is chosen.

A possible synthesis route for derivatives of ginkgolide B according to the invention is as follows:

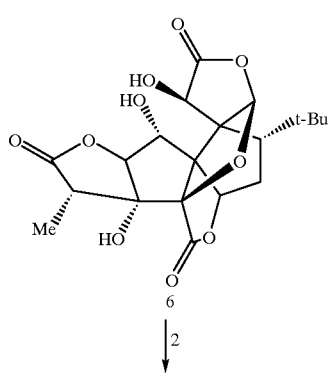

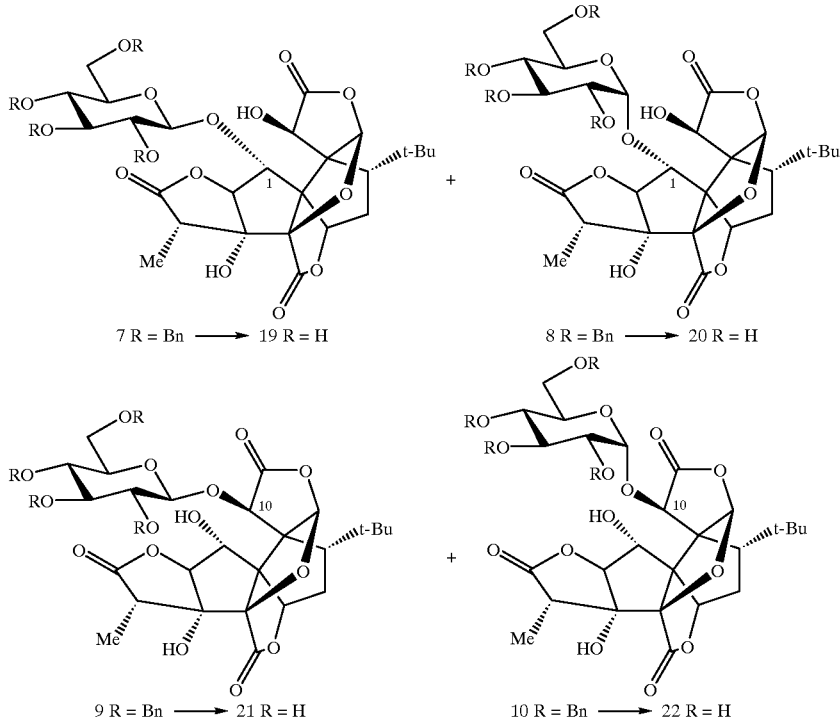

In order to obtain the monoglucosylated derivatives of ginkgolide B (6), photolytic conditions for the glycosylation reaction will preferably be chosen by using approximately 1 to 1.35 equivalents of glucosyl diazirine 2 per ginkgolide equivalent. The debenzylation of the monoglycosylated derivatives 7, 8, 9 and 10 in order to produce compounds 19, 20, 21 and 22 respectively is carried out as previously described for the debenzylation of compound 4.

The monoglycosylated derivatives of ginkgolide B are obtained in the same manner from glycosyl diazirines other than 2, or by starting from another glycosylating reagent and by using a glycosylation reaction as described in the literature. The deprotection stages following the glycosylation reaction remain the same.

If the diglucosylated derivatives of ginkgolide B are desired to be obtained, the following synthesis route can be used, for example:

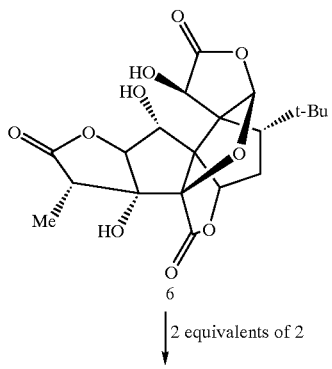

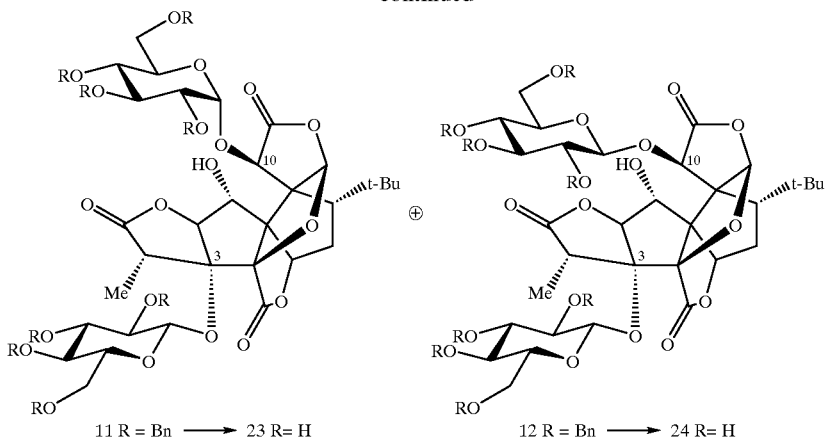

11 R = Bn ⟶ 23 R= H        12 R = Bn ⟶ 24 R= H

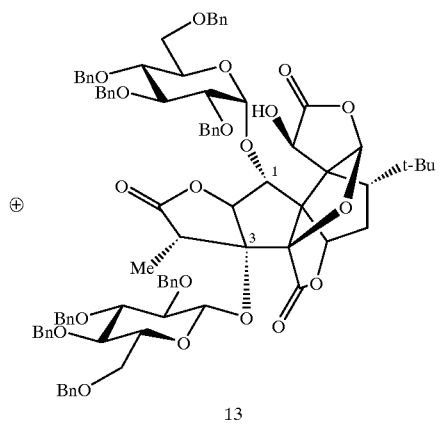

13

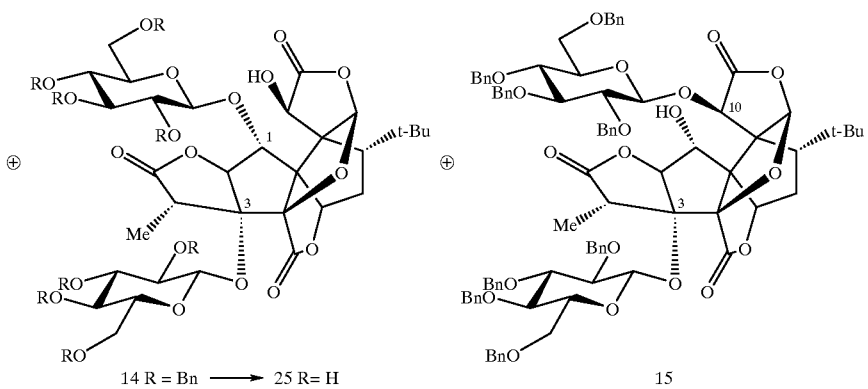

14 R = Bn ⟶ 25 R= H        15

In order to obtain diglycosylated derivatives of ginkgolide B (6), 6 is reacted for 1 hour at 30° C. in THF with 1 equivalent of glucosyl diazirine 2, then another 1 equivalent of glucosyl diazirine 2 is added and allowed to react under the same conditions for 17 hours. A mixture of diglucosylated derivatives 11, 12, 13, 14 and 15 is then obtained. These derivatives can then be debenzylated by hydrogenation with 10% Pd/C in MeOH.

The diglycosilated derivatives of ginkgolide B are obtained in the same manner from glycosyl diazirines other than 2, or by starting from another glycosylating reagent and by using a glycosylation reaction as described in the literature. The deprotection stages following the glycosylation reaction remain the same.

In order to obtain triglucosylated derivatives of ginkgolide B, the following synthesis route will be used:

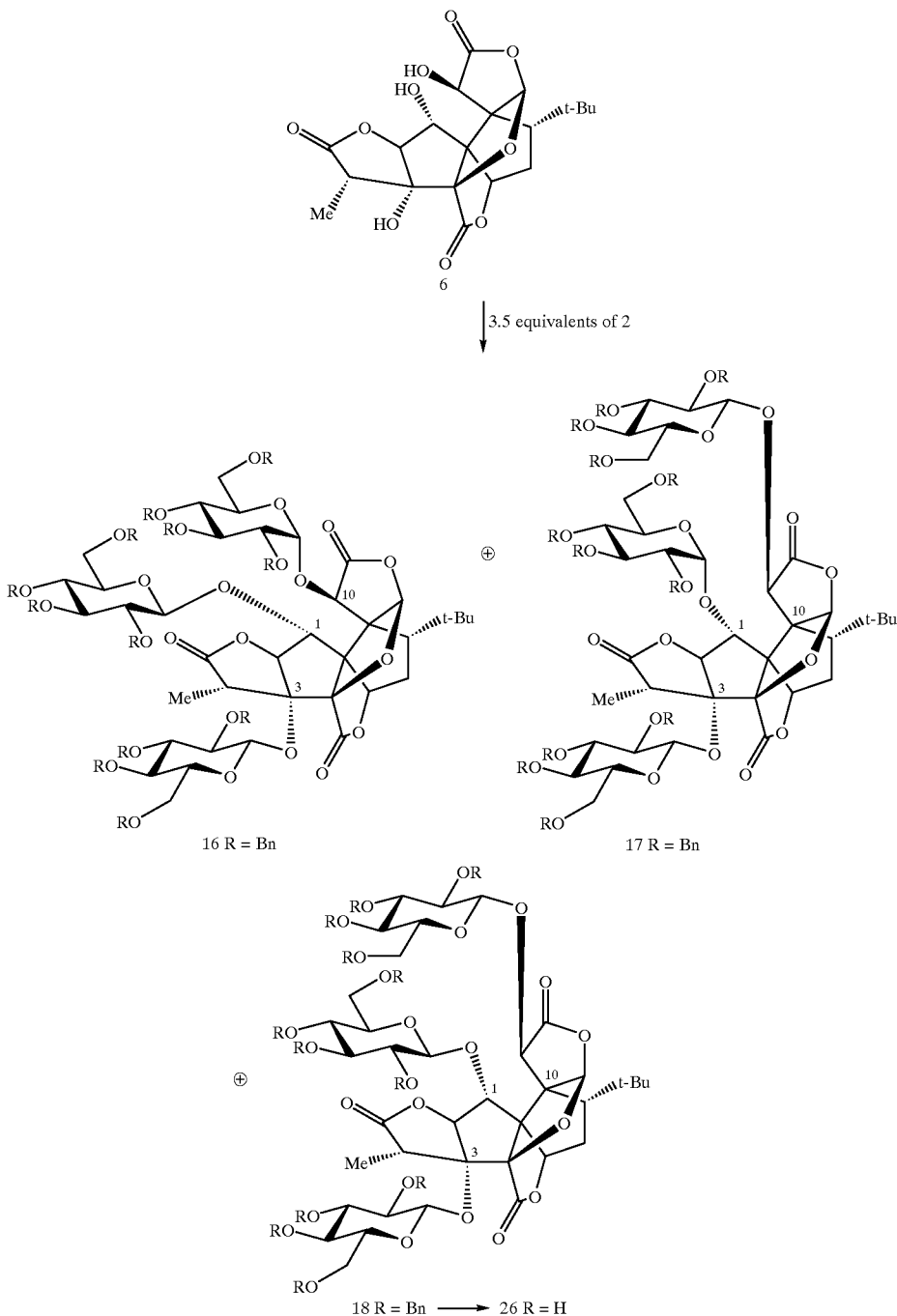

Triglucosylated derivatives of ginkgolide B (6) are obtained by reacting 6 with at least 3.5 equivalents of glucosyl diazirine 2 in THF at 25° C., the addition of 2 being carried out twice separated by an interval of 24 hours, for example. They are then allowed to react for approximately one day and 1,3,10-O-(2,3,4,6-tetra-O-benzyl-β-D-glucopyranosyl)ginkgolide B (18) is obtained in the majority. 1,3-O-(2,3,4,6-tetra-O-benzyl-α-D-glucopyranosyl)-10-O-(2,3,4,6-tetra-O-benzyl-β-D-glucopyranosyl)ginkgolide B (16) and 1-O-(2,3,4,6-tetra-O-benzyl-α-D-glucopyranosyl)-3,10-O-(2,3,4,6-tetra-O-benzyl-β-D-glucopyranosyl)ginkgolide B (17) are also obtained. 18 can then be debenzylated by hydrogenation with 10% Pd/C in MeOH and 1,3,10-O-(β-D-glucopyranosyl)ginkgolide B (26) is then obtained. By using the same method, 16 and 17 can be debenzylated in order to obtain the corresponding debenzylated derivatives.

The triglycosylated derivatives of ginkgolide B are obtained in the same manner by starting from glycosyl diazirines other than 2, or starting from another glycosylating reagent and by using a glycosylation reaction as described in the literature. The deprotection stages following the glycosylation reaction remain the same.

Ginkgolide C can be glycosylated in a manner similar to that used for ginkgolides A or B. A person skilled in the art will choose the stoichiometry of glycosyl diazirine or of glycosylating reagent as a function of the desired degree of glycosylation (mono-, di-, tri- or tetraglycosylated derivative).

In the same manner, the processes previously described could be applied to ginkgolides J and M in order to produce glycosylated derivatives of the latter, or to alkoxylated derivatives of ginkgolides in order to produce the corresponding glycosylated compounds.

The compounds according to the invention have useful pharmacological properties and can for example be used to treat vascular disorders, and in particular cardiovascular disorders. A subject of the invention is therefore also all the glycosylated derivatives of ginkgolides A, B, C, J and M, or glycosylated derivatives of alkoxylated ginkgolides mentioned previously as medicaments, as well as pharmaceutical compositions comprising at least one of these compounds as active ingredient.

The invention therefore relates to pharmaceutical compositions containing a compound according to the invention in combination with a pharmaceutically acceptable support appropriate to the chosen administration method (for example oral, intravenous, intraperitoneal, intramuscular, transdermic or subcutaneous). These pharmaceutical compositions can be in the form of solids, liquids, liposomes or lipidic micellae.

The pharmaceutical compositions according to the invention can be in the form of solids such as, for example, powders, pills, granules, tablets, liposomes, gelatin capsules or suppositories. The pill, tablet or gelatin capsule can be coated in a substance capable of protecting the composition from the action of gastric acid or enzymes in the stomach of the subject for a period of time sufficient to allow this composition to pass in a non-digested form into the small intestine of the latter. The compound can also be administered according to a sustained release process (for example, a sustained release composition or an infusion pump). The appropriate solid supports can be, for example, calcium phosphate, magnesium stearate, magnesium carbonate, talc, sugars, lactose, dextrin, starch, gelatin, cellulose, methyl cellulose, sodium carboxymethyl cellulose, polyvinylpyrrolidine and wax. The pharmaceutical compositions containing a compound according to the invention can therefore also be present in liquid form such as, for example, solutions, emulsions, suspensions or a sustained release formulation. The appropriate liquid supports can be, for example, water, organic solvents such as glycerol or glycols such as polyethylene glycol, similarly their mixtures, in varying proportions, in water.

The invention moreover relates to the use of one of these derivatives to produce a medicament intended to treat vascular diseases, in particular cardiovascular diseases.

The dose of a compound according to the present invention, envisaged for the treatment of the diseases or disorders mentioned above, varies according to the administration method, the age and body weight of the subject to be treated as well as the state of the latter, and it is decided definitively by the attending doctor or vet. Such a quantity determined by the attending doctor or vet is called here "effective therapeutic quantity".

Unless they are defined in another manner, all the technical and scientific terms used here have the same meaning as that commonly understood by an ordinary specialist in the field to which this invention belongs. Similarly, all publications, patent applications, all patents and other references mentioned here are incorporated by way of reference.

The following examples are presented to illustrate the above procedures and should in no event be considered as limiting the scope of the invention.

EXAMPLES

For all the examples which follow, the products already described retain the numbers as indicated above. The shifts in the NMR signals are given in ppm.

Example 1

3-O-(β-D-glucopyranosyl)ginkgolide A (5)

1.1. 10-O-acetyl-ginkgolide A (1):

Ginkgolide A (85 mg, 0.208 mmol) in pyridine (0.75 ml) was treated with $Ac_2O$ (82 μl, 0.87 mmol) and reacted for 20 hours at 25° C. under agitation. After the addition of ethanol, followed by evaporation, and flash chromatography (eluant hexane/acetone 6:4), 1 was obtained (88 mg, 94%). IR ($CHCl_3$): 3483, 2960, 1780, 1602, 1372, 1325, 1152, 1125, 1104, 1084, 1062, 994, 940, 899.

NMR $^1H$ (200 MHz, acetone ($D_6$)): 6.29 (s, H-C(10)); 6.19 (s, H-C(12)); 5.31 (s, HO-C(3)); 5.04–5.01 (m, H-C (6)); 4.92 (dd, J=7.5 Hz, 9.1 Hz, H-C(2)); 3.15 (q, J=7.1 Hz, H-C(14)); 3.03 (dd, J=7.5 Hz, 14.9 Hz, H-C(1)); 2.25 (s, AcO); 2.24–1.86 (m, H-C(1), H-C(7), H'-C(7), H-C(8)); 1.29 (d, J=7.1 Hz, Me-C(14)); 1.12 (s, tBu).

1.2. 10-O-acetyl-3-O-(2,3,4,6-tetra-O-benzyl-β-D-glucopyranosyl)ginkgolide A (3):

1 as obtained in Stage 1.1. (59 mg, 0.131 mmol), in THF (6.0 ml), was treated with a solution of 1-azi-2,3,4,6-tetra-O-benzyl-1-deoxy-D-glucopyranose (2) (95 mg, 0.172 mmol) and agitated for one hour and 30 minutes at 30° C. After evaporation and crystallization (hexane/$CH_2Cl_2$/AcOEt mixture), 3 was obtained (108.5 mg, 85%). Using HPLC (hexane/AcOEt 4:1), another 9.8 mg of 3 (8%) was recovered from the mother solution. M.p. 222° C.

IR ($CHCl_3$): 3066, 3008, 2967, 2874, 1801, 1605, 1497, 1454, 1406, 1373, 1323, 1276, 1116, 1074, 997, 957, 900.

NMR $^1H$ (300 MHz, acetone ($D_6$)): 7.44–7.22 (m, 20 H); 6.34 (s, H-C(10)); 6.21 (s, H-C(12)); 5.60 (dd, J=8.4 Hz, 9.0 Hz, H-C(2)); 5.01 (d, J=3.1 Hz, H-C(6)); 4.92 (d, J=10.6 Hz), 4.82 (s), 4.77 (d, J=10.9 Hz, 4 PhCH); 4.72 (d, J=7.5 Hz, H-C(1')); 4.66 (d, J=11.2 Hz), 4.65 (d, J=11.5 Hz), 4.61 (d, J=10.6 Hz), 4.51 (d, J=11.8 Hz, 4 PhCH); 3.81–3.75 (m, H-C(4'), H-C(6'), H'-C(6')); 3.60 (t, J=9.0 Hz, H-C(3')); 3.41 (dd, J=7.5 Hz, 9.0 Hz, H-C(2')); 3.34 (dt, J=2.2 Hz, 9.6 Hz, H-C(5')); 3.20 (q, J=6.8 Hz, H-C(14)); 3.17 (dd, J=7.5 Hz, 14.9 Hz, H-C(1)); 2.25 (s, AcO); 2.21–2.16 (m, 2 H); 2.01–1.89 (m, 2H); 1.43 (d, J=6.8 Hz, Me-C(14)); 1.11 (s, tBu).

NMR $^{13}C$ (100 MHz, acetone ($D_6$)): 176.4 (s); 170.4 (s); 169.6 (s); 169.1 (s); 140.0(s); 139.9(s); 139.7 (2s); 129.1–128.1 (several d); 111.8 (d); 101.9 (s); 99.3 (d); 94.4 (s); 85.7 (d); 85.2 (d); 82.6 (d); 82.2 (d); 78.0 (d); 75.9 (t); 75.7 (d); 75.5 (t); 75.2 (t); 73.9 (t); 70.3 (d); 69.6 (s); 68.3 (t); 66.8 (s); 49.8 (d); 41.9 (d); 38.1 (t); 37.5 (t); 32.8 (s); 20.5 (q); 8.4 (q).

Elemental analysis: C 68.87%, H 6.21% (theoretical values: C 69.12% and H 6.21%).

1.3. 3-O-(2,3,6-tetra-O-benzyl-β-D-glucopyranosyl) ginkgolide A (4):

3 as obtained in Stage 1.2. (110 mg, 0.11 mmol), placed in MeOH (5 ml) and $CH_2Cl_2$ (2 ml), was treated with a saturated solution of $NH_3$ in MeOH (1.2 ml) and agitated at 25° C. for one hour and 30 minutes. After evaporation and flash chromatography (eluant hexane/acetone 3:2) and HPLC, 48 mg of 4 was obtained (46%).

IR ($CHCl_3$): 3290, 3008, 2967, 2874, 1794, 1497, 1454, 1362, 1324, 1144, 1073, 1028, 995, 953, 903.

NMR $^1H$ (300 MHz, acetone ($D_6$)): 7.43–7.25 (m, 20 H); 6.13 (s, H-C(12)); 5.95 (d, J=4.4 Hz, HO-C(10)); 5.54 (t, J=8.4 Hz, H-C(2)); 5.22 (d, J=4.1 Hz, H-C(10)); 4,95-4.91 (m, H-C(6), Ph-CH), 4.82 (s), 4.77 (d, J=11.2 Hz, 3 PhCH); 4.72 (d, J=7.5 Hz, H-C(1')); 4.65 (d,J=13.1 Hz), 4.65 (d, J=11.5 Hz), 4.61 (d, J=10.9 Hz), 4.52 (d, J=11.8 Hz, 4 PhCH); 3.81–3.74 (m, H-C(4'), H-C(6'), H'-C(6')); 3.61 (t, J=9.0 Hz, H-C(3')); 3.43–3.33 (m, H-C(2'), H-C(5')); 3.21 (q, J=6.8 Hz, H-C(14)); 3.03 (dd, J=7.5 Hz, 14.9 Hz, H-C(1)); 2.25 (s, AcO); 2.30–1.91 (m, 4 H); 1.43 (d, J=6.8 Hz, Me-C(14)); 1.15 (s, tBu).

1.4. 3-O-(βD-glucopyranosyl)ginkgolide A (5):

4as obtained in Stage 1.3. (47 mg, 0.05 mmol), mixed with 10% Pd/C (90 mg), was hydrogenated in MeOH (10 ml) for 72 hours under a pressure of 3 atm. After filtration, evaporation, and flash chromatography (eluant AcOEt/MeOH/H$_2$O 8.5:1.5:1), 5 was obtained (25 mg, 84%).

NMR $^1$H (300 MHz, CD$_{30}$OD): 6.07 (s, H-C(12)); 5.50 (dd, J=8.1 Hz, 9.0 Hz, H-C(2)); 5.04 (s, H-C(10)); 4.90 (d, J=3.4 Hz, H-C(6)); 4.50 (d, J=7.5 Hz, H-C(1')); 3.75 (dd, J=2.2 Hz, 12.1 Hz, H-C(6')); 3.60 (dd, J=4.8 Hz, 12.1 Hz, H'-C(6')); 3.35–3.15 (m, 5H); 2.93 (dd, J=7.5 Hz, 14.9 Hz, H-C(1)); 2.29–2.11 (m, 2H); 2.00–1.85 (m, 2 H); 1.33 (d, J=6.8 Hz, Me-C(14)); 1.10 (s, tBu).

Example 2

Treatment of ginkgolide B (6) with 1, 2 or 3,5 equivalents of 1-azi-2,3,4,6-tetra-O-benzyl-1-deoxy-D-glucopyranose (2)

2.1. Treatment with 1 equivalent of azirine:

Ginkgolide B (6) (134.0 mg, 0.31 mmol) in THF (4.0 ml) was cooled down to −75° C., treated with a solution of 1-azi-2,3,4,6-tetra-O-benzyl-1-deoxy-D-glucopyranose (2) (177 mg, 0.32 mmol) in THF (1.5 ml), and irradiated (Philips HPK-125 high-pressure mercury lamp) for 1 hour at −70° C. The mixture was then heated at 23° C. and evaporated. After filtration on silica (eluant AcOEt) and HPLC (eluant hexane/AcOEt 2:1), 7 (140.3 mg, 47%), 8 (23.0 mg, 8%), 9 (82.4 mg, 27%), and 10 (29.8 mg, 10%) were then obtained.

2.2. Treatment with 2 equivalents of azirine:

Ginkgolide B (6) (97.2 mg, 0.229 mmol), in THF (2.0 ml), was treated with a solution of 1-azi-2,3,4,6-tetra-O-benzyl-1-deoxy-D-glucopyranose (2) (135 mg, 0.245 mmol) in THF (1.0 ml) at 30° C., then one hour later with a second solution of 2 (119.0 mg, 0.216 mmol) in THF (0.9 ml). The reaction medium is then agitated for 17 hours at 30° C. After evaporation, filtration on silica (eluant AcOEt) and HPLC (eluant hexane/AcOEt 2:1), 7 (26.3 mg, 12%), 9 (35.8 mg, 17%), 10 (34.9 mg, 16%), 11 (20.7 mg, 6%), 12 (32.6 mg, 10%), 13 (8.9 mg, 3%), 14 (15.6 mg, 5%), 15 (5.6 mg, 2%), a mixture of 16 and 17 (8.1 mg, 2%) and 18 (6.7 mg, 2%) were obtained.

2.3. Treatment with 3.5 equivalents of azirine:

Ginkgolide B (6) (27.0 mg, 0.064 nimol) was treated with a solution of 1-azi-2,3,4,6-tetra-O-benzyl-1-deoxy-D-glucopyranose (2) (60.0 mg, 0.109 mmol) in THF (1.3 ml) at 25° C., then 24 hours later by a second solution of 2 (60.0 mg, 0.109 mmol) in THF (1.3 ml). The reaction medium is then agitated for 20 hours at 25° C. After evaporation, filtration on silica (eluant AcOEt) and HPLC (eluant hexane/AcOEt 4:1), 11 (21.9 mg, 24%), 16 (18.4 mg, 15%), 17 (16.0 mg, 13%) and 18 (51.0 mg, 42%) were obtained.

2.4. IR and NMR data for products 7 to 18:

1-O-(2,3,4,6-tetra-O-benzyl-β-D-glucopyranosyl) ginkgolide B (7)

IR (CHCl$_3$): 3564, 3451, 3328, 3090, 3066, 3007, 2966, 2913, 2873, 1952, 1794, 1604, 1497, 1454, 1405, 1360, 1324, 1310, 1172, 1143, 1070, 1028, 962, 906.

NMR $^1$H (500 MHz, acetone (D$_6$)): 7.42–7.24 (m, 20 H); 6.02 (s, H-C(12)); 5.60 (d, J=3.7 Hz, H-C(6)); 5.50 (s, exchanged by D$_{20}$, HO-C(3)); 4.98–4.96 (m, 2 H); 4.87 (d, J=11.2 Hz, PhCH); 4.84–4.79 (m, 3 H); 4.76 (d, J=11.3 Hz), 4.67 (d, J=11.1 Hz), 4.66 (d, J=12.3 Hz), 4.60 (d, J=12.3 Hz, 4 PhCH); 3.83 (dd, J=2.0 Hz, 11.0 Hz, H-C(6')); 3.78 (dd, J=3.9 Hz, 11.0 Hz, H'-C(6')); 3.71 (t, J=8.9 Hz, H-C(4')); 3.66 (t, J=8.5 Hz, H-C(3')); 3.51 (ddd, J=1.9 Hz, 3.9 Hz, 9.5 Hz, H-C(5')); 3.46 (t, J=8.1 Hz, H-C(2')); 3.06 (q, J=7.5 Hz, H-C(14)); 2.10 (ddd, J=3.9 Hz, 13.7 Hz, 13.9 Hz, H-C(7)); 2.03 (dd, J=4.7 Hz, 13.5 Hz, H'-C(7)); 1.93 (dd, J=4.7 Hz, 14.0 Hz, H-C(8)); 1.29 (d, J=7.5 Hz, Me-C(14)); 1.11 (s, t-Bu).

NMR $^{13}$C (125 MHz, acetone (D$_6$)): 176.5 (s); 173.9 (s); 171.7 (s); 140.1 (s); 139.9 (s); 139.8 (s); 139.8 (s); 129.3–128.4 (several d) 110.1 (d); 104.0 (d); 103.3 (s); 95.5 (d); 86.2 (s); 85.8 (d); 83.7 (d); 83.4 (d); 80.2 (d); 79.8 (d); 76.1 (t); 76.0 (d); 75.4 (2t); 74.9 (s); 74.2 (t); 70.4 (d); 70.2 (s); 69.7 (t); 50.6 (d); 42.1 (d); 37.8 (t); 33.3 (s); 10.4 (q).

1-O-(2,3,4,6-tetra-O-benzyl-α-D-glucopyranosyl) ginkgolide B (8)

IR (CHCl$_3$): 3566, 3342, 3089, 3069, 3007, 2966, 2873, 1795, 1603, 1497, 1454, 1406, 1357, 1326, 1284, 1168, 1100, 1068, 1029, 986, 962, 902.

NMR $^1$H (400 MHz, acetone (D$_6$)): 7.34–7.18 (20 H); 6.08 (s, H-C(12)); 5.62 (d, J=3.5 Hz, H-C(6)); 5.36 (s, exchanged by D$_2$O, HO-C(3)); 4.93 (d, J=11.2 Hz, PhCH), 4.87–4.81 (m, 5 H); 4.79 (d, J=11.6 Hz), 4.60 (d, J=12.2 Hz), 4.57 (d, J=12.1 Hz, 3 PhCH); 4.21 (dt, J=3.0 Hz, 10.1 Hz, H-C(5')); 3.90 (t, J=9.4 Hz, H-C(3')); 3.70 (d, J=3.1 Hz, 2 H-C(6')); 3.61 (dd, J=3.7 Hz, 9.6 Hz, H-C(2')); 3.57 (dd, J=9.1 Hz, 10.1 Hz, H-C(4')); 3.12 (q, J=7.2 Hz, H-C(14)); 2.20 (dd, J=5.2 Hz, 13.4 Hz, H-C(7)); 2.19–2.13 (m, H'-C(7));

1.92 (dd, J=5.2 Hz, 13.5 Hz, H-C(8)); 1.28 (d, J=7.2 Hz, Me-C(14)); 1.14 (s, t-Bu).

NMR $^{13}$C (100 MHz, acetone (D$_6$)): 176.2 (s); 173.9 (s); 171.1 (s); 140.1 (s); 139.7 (s); 139.5 (2s); 129.2–128.2 (several d); 110.5 (d); 101.0 (s); 96.3 (d); 93.7 (d); 85.4 (s); 82.3 (d); 81.1 (d); 80.1 (d); 79.8 (d); 78.9 (d); 75.7 (2t); 73.9 (t); 73.9 (t); 73.6 (s); 72.5 (d); 70.1 (d); 69.8 (s, t); 50.0 (d); 42.5 (d); 37.6 (t); 33.1 (s); 8.8 (q).

10-O-(2,3,4,6-tetra-O-benzyl-β-D-glucopyranosyl) ginkgolide B (9)

IR (CHCl$_3$): 3565, 3490, 3090, 3067, 3008, 2966, 2944, 2915, 2872, 1951, 1785, 1605, 1497, 1454, 1406, 1361, 1327, 1314, 1280, 1163, 1098, 1028, 988, 967, 926.

NMR $^1$H (500 MHz, acetone (D$_6$)): 7.51–7.08 (m, 20 H); 6.12 (s, H-C(12)); 5.36–5.35 (m, H-C(6)); 5.28 (s, exchanged by D$_2$O, HO-C(3)); 5.04 (d, J=11.8 Hz), 4.92 (d, J=11.2 Hz), 4.81 (d, J=10.3 Hz), 4.80 (d, J=11.7 Hz), 4.79 (d, J=11.0 Hz), 4.70 (d, J=11.0 Hz), 4.69 (d, J=12.0 Hz), 4.57 (d, J=12.0 Hz, 8 PhCH); 3.87 (t, J=8.6 Hz, H-C(3')); 3.83 (dd, J=3.9 Hz, 11.2 Hz, H-C(6')); 3.80 (t, J=8.7 Hz, H-C(4')); 3.71 (dd, J=2.0 Hz, 11.5 Hz, H'-C(6')); 3.70–3.67 (m, H-C(5')); 3.64 (dd, J=7.5 Hz, 8.4 Hz, H-C(2')); 3.09 (q, J=7.0 Hz, H-C(14)); 2.05–1.96 (m, H-C(7), H-C(8)); 1.86–1.82 (m, H'-C(7)); 1.28 (d, J=7.0 Hz, Me-C(14)); 1.06 (s, t-Bu).

NMR $^{13}$C (125 MHz, acetone (D$_6$)): 176.8 (s); 171.0 (s); 170.3 (s); 139.6 (s); 139.4 (s); 139.4 (s); 139.4 (s); 129.3–127.9 (several d); 110.3 (d); 100.5 (d); 99.7 (s); 93.5 (d); 85.9 (d); 83.9 (s); 81.6 (d); 79.5 (d); 78.7 (d); 75.9 (d); 75.6 (t); 75.3 (t); 75.2 (d); 74.9 (d); 74.4 (t); 74.2 (t); 73.3 (s); 69.4 (t); 69.0 (s); 50.1 (d); 42.9 (d); 37.6 (t); 32.8 (s); 8.2.(q).

10-O-(2,3,4,6-tetra-O-benzyl-α-D-glucopyranosyl) ginkgolide B (10)

IR (CHCl$_3$): 3566, 3388, 3090, 3067, 3008, 2964, 2916, 2874, 1952, 1790, 1604, 1497, 1454, 1406, 1363, 1326, 1312, 1165, 1103, 1069, 1028, 1005, 987, 966, 920.

NMR $^1$H (400 MHz, acetone (D$_6$)): 7.39–7.06 (20 H); 6.25 (s, H-C(12)); 5.42 (d, J=3.9 Hz, H-C(6)); 5.31 (s, replaced by D$_2$O, HO-C(3)); 5.07 (d, J=10.8 Hz), 4.83 (d, J=10.7 Hz), 4.81 (d, J=11.0 Hz), 4.77 (d, J=11.2 Hz), 4.75 (d, J=11.3Hz), 4.62 (d, J=10.7Hz), 4.60 (d, J=11.9Hz), 4.52 (d,J=11.9Hz, 8 PhCH); 3.88–3.70 (m, 5 H); 3.55 (dd, J=1.4 Hz, 10.7 Hz, H'-C(6')); 3.07 (q, J=7.0 Hz, H-C(14)); 2.24 (dd, J=4.3 Hz, 13.4 Hz, H-C(7)); 2.04–1.96 (m, H'-C(7)); 1.85 (dd, J=4.1 Hz, 14.5Hz, H-C(8)); 1.28 (d,J=7.0Hz, Me-C(14)); 1.18 (s, t-Bu).

NMR $^{13}$C (100 MHz, acetone (D$_6$)): 176.6 (s); 172.9 (s); 171.0 (s); 139.6 (s); 139.5 (s); 139.4 (s); 137.6 (s); 129.4–128.3 (several d); 110.7 (d); 99.6 (s); 96.6 (d); 93.3 (d); 83.4 (s); 81.8 (d); 80.8 (d) 79.2 (d); 77.9 (d); 76.1 (t); 75.8 (t); 75.7 (t); 74.7 (d); 74.1 (t); 73.7 (d); 73.7 (d); 72.9 (s); 69.1 (t); 69.2 (s); 49.6 (d); 42.9 (d); 38.4 (t); 33.1 (s); 8.2 (q).

3-O-(2,3,4,6-tetra-O-benzyl-β-D-glucopyranosyl)-10-O-(2,3,4,6-tetra-O-benzyl-α-D-glucopyranosyl) ginkgolide B (11)

IR (CHCl$_3$): 3395, 3090, 3067, 3008, 2923, 2874, 1951, 1793, 1606, 1497, 1454, 1406, 1362, 1325, 1275, 1163, 1070, 1028, 987, 920, 902.

NMR $^1$H (300 MHz, acetone (D$_6$)): 7.46–7.20 (m, 40 H); 6.30 (s, H-C(12)); 5.34 (d, J=3.7 Hz, H-C(6)); 5.10 (d, J=10.6 Hz), 4.93 (d, J=10.6 Hz), 4.84 (d, J=10.6 Hz), 4.814.50 (m, 16 PhCH); 3.89–3.71 (m, 8 H); 3.67 (t, J=8.7 Hz, H-C(3")); 3.55 (d, J=10.0 Hz, H'-C(6')); 3.43–3.40 (m, H-C(5 41 )); 3.38 (dd, J=7.5 Hz, 8.7 Hz, H-C(2")); 3.12 (q, J=6.8 Hz, H-C(14)); 2.22 (dd, J=3.9 Hz, 12.9 Hz, H-C(7)); 1.98 (ddd, J=4.0 Hz, 13.1 Hz, 14.2 Hz, H'-C(7));

1.85 (dd, J=3.7 Hz, 14.3 Hz, H-C(8)); 1.44 (d, J=6.8 Hz, Me-C(14)); 1.17 (s, t-Bu).

3,10-O-(2,3,4,6-tetra-O-benzyl-β-D-glucopyranosyl) ginkgolide B (12)

IR (CHCl$_3$): 3492, 3090, 3067, 3008, 2873, 1951, 1793, 1606, 1497, 1454, 1406, 1361, 1326, 1314, 1279, 1152, 1072, 1028, 988, 968, 903.

NMR $^1$H (300 MHz, acetone (D6)): 7.46–7.24 (m, 40 H); 6.17 (s, H-C(12)); 5.30 (s, H-C(6)); 5.22 (d, J=7.2 Hz, H-C(2)); 5.05 (d, J=11.5 Hz), 4.93 (d, J=11.2Hz), 4.81–4.64 (m), 4.60 (d, J=12.1 Hz), 4.51 (d, J=11.8Hz, 16 PhCH); 3.89 (t, J=8.4 Hz, H-C(3')); 3.86–3.63 (m, irradiation at 5.27 →d, J=9.0 Hz, H-C(2'), 8 H); 3.43-3.40 (m, H-C(5")); 3.40 (dd, J=7.8 Hz, 8.7 Hz, H-C(2")); 3.12 (q, J=6.8, H-C(14)); 2.02–1.80 (m, H-C(8), H-C(7), H'-C(7)); 1.44 (d, J=6.5 Hz, Me-C(14)); 1.05 (s, t-Bu).

1-O-(2,3,4,6-tetra-O-benzyl-α-D-glucopyranosyl)-3-O-(2,3,4,6-tetra-O-benzyl-β-D-glucopyranosyl) ginkgolide B (13)

IR (CHCl$_3$): 3392, 3090, 3066, 3008, 2917, 2874, 1952, 1795, 1605, 1497, 1454, 1406, 1360, 1325, 1313, 1284, 1154, 1070, 1028, 986, 961, 923.

NMR $^1$H (300 MHz, acetone (D$_6$)): 7.45–7.22 (m, 40 H); 6.13 (s, H-C(12)); 5.58 (m, H-C(6)); 4.98 (d, J=11.2 Hz), 4.96–4.75 (m, 9 PhCH); 4.65–4.58 (m, irradiation at 5.28→m, H-C(1), 6 PhCH); 4.48 (d, J=11.5 Hz, PhCH); 4.21 (dt, H-C(5'); 3.98 (t, J=9.6 Hz, H-C(3')); 3.72–3.67 (m, 5 H); 3.62 (dd, J=3.7 Hz, 9.6 Hz, H-C(2')); 3.58 (t, J=9.0 Hz, H-C(4')); 3.47 (t, J=9.0 Hz, irradiation at 3.35→d, J=9.3 Hz, H-C(3")); 3.35 (dd, J=7.5 Hz, 9.0 Hz, H-C(2")); 3.15 (q, J=7.0 Hz, H-C(14)); 3.04 (dt, H-C(5")); 2.16–2.14 (m, H-C(7)); 1.93–1.84 (m, H'-C(7)); 1.39 (d, J=6.9 Hz, Me-C(14));1.36–1.29 (m, H-C(8)); 1.13 (s, t-Bu).

1,3-O-(2,3,4,6-tetra-O-benzyl-β-D-glucopyranosyl) ginkgolide B (14)

IR (CHCl$_3$): 3462, 3090, 3066, 3008, 2873, 1952, 1796, 1702, 1604, 1497, 1454, 1406, 1361, 1322, 1278, 1177, 1148, 1082, 1028, 987, 956, 923, 905.

NMR $^1$H (300 MHz, acetone (D$_6$)): 7.44–7.16 (m, 40 H); 6.15 (s, H-C(12)); 5.43–5.42 (m, H-C(6)); 4.97 (d, J=11.5 Hz), 4.90 (d, J=10.9 Hz), 4.85 (d, J=11.2 Hz), 4.83 (d, J=11.2 Hz), 4.80–4.68 (m), 4.62 (d, J=12.5 Hz), 4.61 (d, J=12.1 Hz), 4.48 (d, J=11.8 Hz, 16 PhCH); 3.93 (d, J=2.2 Hz, H-C(6'), H'-C(6')); 3.83 (dd, J=9.0 Hz, 9.7 Hz, H-C(4')); 3.74–3.63 (m, irradiation at 3.83→m, H-C(3'), 3 H); 3.55–3.46 (m, irradiation at 3.83→m, H-C(5'), irradiation at 4.81→m, H-C(2'), irradiation at 3.37→m, H-C(3")); 3.37 (dd, J=7.5 Hz, 9.0 Hz, irradiation at 4.65→d, J=9.0 Hz, H-C(2")); 3.25 (m, H-C(5")); 3.22 (q, J=6.8 Hz, H-C(14)); 1.89 (dd, J=6.5 Hz, 12.4 Hz, H-C(7));

1.41 (d, J=7.1 Hz, Me-C(14)); 1.09 (s, t-Bu).

3-O-(2,3,4,6-tetra-O-benzyl-α-D-glucopyranosyl)-10-O-(2,3,4,6-tetra-O-benzyl-β-D-glucopyranosyl) ginkgolide B (15)

IR (CHCl$_3$): 3534, 3090, 3066, 3008, 2926, 2874, 1951, 1795, 1706, 1603, 1497, 1454, 1404, 1361, 1324, 1313, 1261, 1139, 1072, 1028, 989, 966, 904.

NMR $^1$H (300 MHz, acetone (D$_6$)): 7.43–7.22 (m, 40 H); 6.19 (s, H-C(12)); 5.27 (d, J=3.4 Hz, H-C(6)); 4.97 (d, J=11.8 Hz), 4.93 (d, J=11.8 Hz), 4.92 (d, J=10.6 Hz), 4.87–4.73 (m), 4.68–4.48 (m, 16 PhCH); 3.99–3.94 (m, 1 H); 3.82–3.55 (m, 9 H); 3.39 (dd, J=4.2 Hz, 7.3 Hz, irradiation at 4.80→m, H-C(2')); 3.38 (dd, J=6.5 Hz, 7.3 Hz, 1 H); 3.37 (dd, J=7.8 Hz, 8.7 Hz, irradiation at 4.50→d, J=9.0 Hz, H-C(2")); 3.05 (q, J=6.8 Hz, H-C(14)); 2.16–1.74 (m, 3 H); 1.41 (d, J=6.8 Hz, Me-C(14)); 1.14 (s, tBu).

1,3-O-(2,3,4,6-tetra-O-benzyl-β-D-glucopyranosyl)-10-O-(2,3,4,6-tetra-O-benzyl-α-D-glucopyranosyl) ginkgolide B (16)

IR (CHCl$_3$): 3089, 3066, 3008, 2926, 2872, 1951, 1791, 1709, 1604, 1497, 1454, 1363, 1312, 1279, 1073, 1028, 984, 910.

NMR $^1$H (500 MHz, acetone (D$_6$)): 7.45–7.01 (m, 60 H); 6.05 (s, H-C(12)); 5.44 (d, J=3.6 Hz, H-C(6)); 5.26 (d, J=10.7 Hz), 5.02 (d, J=10.7 Hz), 4.99 (d, J=11.1 Hz), 4.96 (d, J=12.0 Hz), 4.95 (d, J=10.6 Hz), 4.90 (d, J=10.7 Hz), 4.83 (d, J=11.4 Hz), 4.80 (d, J=11.6 Hz), 4.78 (d, J=11.4Hz), 4.77 (d, J=10.7 Hz), 4.69–4.59 (m), 4.48 (d, J=12.6 Hz), 4.47 (d, J=12.0 Hz), 4.45 (d, J=11.3 Hz, 21 PhCH); 4.44 (m, H-C(3")); 4.41 (d, J=12.1 Hz), 4.38 (d, J=11.3 Hz), 4.31 (d, J=12.6 Hz, 3 PhCH); 4.06 (t, J=9.7 Hz, H-C(4')); 4.00 (t, J=9.2 Hz, H-C(3')); 3.99 (m$_c$, H-C(6')); 3.94 (dd, J=4.5 Hz, 10.6 Hz, H-C(2')); 3.73–3.63 (m, H-C(3'"), H-C(5'"), H-(6'"), H'-C(6'"), H-C(5'), H-C(4'")); 3.59–3.55 (m, H-C4"), H-C(6")); 3.45 (dd, J=7.9 Hz, 9.4 Hz, H-C(2")); 3.40 (t, J=7.7 Hz, H-C(2.'")); 3.23 (dd, J=3.7 Hz, 10.9 Hz, H-C(6")); 3.18 (q, J=7.8 Hz, H-C(14)); 3.14 (dd, J=1.6 Hz, 1.0 Hz, H'-C(6")); 2.95 (m$_c$, H-C(5")); 1.76 (dd, J=4.1 Hz, 14.6 Hz, H-C(7)); 1.44 (d, J=7.8 Hz, Me-C(14)); 1.33 (m, H-C(8)); 1.14 (dt, J=4.0 Hz, 14.2 Hz, H'-C(7)); 1.04 (s, t-Bu).

1-O-(2,3,4,6-tetra-O-benzyl- α-D-glucopyranosyl)-3,10-O-(2,3,4,6-tetra-O-benzyl-β-D-glucopyranosyl) ginkgolide B (17)

IR (CHCl$_3$): 3090, 3066, 3008, 2913, 2872, 1951, 1794, 1605, 1497, 1454, 1399, 1360, 1328, 1310, 1279, 1145, 1074, 1028, 1007, 985, 902.

NMR $^1$H (500 MHz, acetone (D$_6$)): 7.42–7.05 (m, 60 H); 6.03 (s, H-C(12)); 5.36 (d, J=3.7 Hz, H-C(6)); 5.17 (d, J=10.6 Hz), 5.03 (d, J=10.9 Hz), 4.99 (d, J=11.7Hz), 4.93 (d, J=11.3Hz), 4.88 (d, J=11.2Hz), 4.85 (d, J=11.0 Hz), 4.80 (d, J=12.5 Hz), 4.78 (d, J=11.2 Hz), 4.74 (d, J=11.2 Hz), 4.70 (d, J=11.0 Hz), 4.66 (d, J=11.9 Hz), 4.62 (d, J=10.5 Hz), 4.60 (d, J=11.0 Hz), 4.51 (d, J=10.5 Hz), 4.50 (d, J=11.7 Hz), 4.49 (d, J=10.6 Hz), 4.47 (m), 4.43 (d, J=12.1 Hz), 4.39 (d, J=11.2 Hz), 4.37 (d, J=12.0 Hz, 24 PhCH); 4.19–4.13 (m, H-C(5'), H-C(4'''), H-C(3')); 3.97 (t, J=7.8 Hz, H-C(2'')); 3.87 (m, H-C(4')); 3.84 (t, J=7.8 Hz, H-C(3'')); 3.82–3.67 (m, 7 H); 3.66 (dd, J=4.4 Hz, 9.6 Hz, H-C(2')); 3.46 (dd, J=2.9 Hz, 10.8 Hz, 1 H); 3.40–3.38 (m, 1H); 3.36 (dd, J=7.6 Hz, 8.9 Hz, H-C(2''')); 3.10 (q, J=7.5 Hz, H-C(14)); 3.07 (m, 1 H); 1.94 (dt, J=4.0 Hz, 14.1 Hz, H-C(7)); 1.75 (dd, J=4.0 Hz, 14.4 Hz, H'-C(7)); 1.36 (dd, J=4.1 Hz, 13.4 Hz, H-(8)); 1.30 (d, J=7.5 Hz, Me-C(14)); 0.94 (s, t-Bu).

1,3,10-O-(2.3,4,6-tetra-O-benzyl-β-D-glucopyranosyl)ginkgolide B (18)

IR (CHCl$_3$): 3090, 3066, 3008, 2913, 2872, 1951, 1792, 1702, 1654, 1606, 1586, 1497, 1454, 1400, 1360, 1314, 1280, 1148, 1074, 1028, 987, 905.

NMR $^1$H (300 MHz, acetone (D$_6$)): 7.50–7.09 (m, 60 H); 6.11 (s, H-C(12)); 5.66(s, H-C(6)); 5.10 (d, J=11.5Hz), 4.99 (d, J=11.2Hz), 4.97 (d, J=11.2Hz), 4.88 (d, J=11.2Hz), 4.86 (d,J=11.2Hz), 4.77 (d,J=11.2Hz), 4.78–4.53 (m), 4.47 (d, J=11.8 Hz), 4.43 (d, J=11.2 Hz, 24 PhCH); 4.10 (t, J=8.1 Hz, irradiation at 5.01→d, J=8.4 Hz, H-C(2'')); 4.00–3.94 (m, irradiation at 3.42→m, H-C(3'''), 1 H); 3.86–3.66 (m, irradiation at 4.10→m, H-C(3''), 9 H); 3.58 (dd, J=7.9 Hz, 9.2 Hz, irradiation at 5.34→d, J=9.0 Hz, H-C(2')); 3.57 (t, J=9.0 Hz, I H); 3.46–3.39 (m, irradiation at 4.83→m, H-C(2'''), 2 H); 3.28 (q, J=7.2 Hz, H-C(14)); 1.91–1.85 (m, 1 H); 1.45 (d, J=7.5 Hz, Me-C(14)); 0.98 (s, tBu).

2.5. 1-O-(β-D-glucopyranosyl)ginkgolide B (19)

A mixture of 7 (73.0 mg, 0.077 mmol) as obtained for example in Stage 2.1. or 2.2., and 10% Pd/C (100 mg) in MeOH (3.0 ml) was hydrogenated for 17 hours under a pressure of 3.5 atm. After filtration and evaporation, 19 (42.7 mg, 94%) was obtained.

NMR $^1$H (400 MHz, acetone(D$_6$)): 6.09 (s, H-C(12)); 5.55–5.35 (m, H-C(6)); 3.85–3.79 (m, H-C(6')); 3.66 (dd, J=5.4 Hz, 11.6, H'-C(6')); 3.47 (t, J=8.8 Hz, H-C(3')); 3.40–3.33 (m, H-C(4'), H-C(5')); 3.28 (dd, J=7.8 Hz, 8.9 Hz, H-C(2')); 3.09 (q, J=7.2 Hz, H-C(14)); 2.25–2.18 (m, H-C(7), H'-C(7)); 1.94 (dd, J=6.5 Hz, 12.4 Hz, H-C(8)); 1.25 (d, J=7.4 Hz, Me-C(14)); 1.26 (s, t-Bu).

NMR $^{13}$C (100 MHz, acetone (D$_6$)): 176.4 (s); 173.9 (s); 170.9 (s); 110.6 (d); 100.8 (s); 94.0 (d); 85.5 (s); 83.2 (d); 80.1 (d); 77.8 (2d); 75.0 (d); 73.2 (s); 71.5 (d); 70.4 (d); 69.6 (s); 62.8 (t); 50.0 (d); 42.4 (d); 37.7 (d); 33.1 (s); 31.9 (3q); (8.8 (q).

2.6. 1-O-(α-D-glucopyranosyl)ginkgolide B (20):

A mixture of 8 (20.1 mg, 0.021 mmol) as obtained for example in Stage 2.1., and 10% Pd/C (50 mg) in MeOH (3.0 ml) was hydrogenated for 17 hours under a pressure of 2.1 atm. After filtration and evaporation, 20 (6.5 mg, 52%) was obtained.

NMR $^1$H (300 MHz, CD$_3$OD): 6.00 (s, H-C(12)); 5.67 (d, J=3.1 Hz, H-C(6)); 3.90 (ddd, J=2.6 Hz, 3.4 Hz, 9.6 Hz, H-C(5')); 3.81 (dd, J=2.5 Hz, 12.1 Hz, H-C(6')); 3.73 (dd, J=3.7 Hz, 11.8 Hz, H'-C(6')); 3.61 (dd, J=9.0 Hz, 9.9 Hz, H-C(3')); 3.47 (dd, J=3.7 Hz, 9.9 Hz, irradiation at 5.11→d, J=9.7 Hz, H-C(2')); 3.44 (dd, J=9.0 Hz, 9.9 Hz, H-C(4')); 3.07 (q, J=7.2 Hz, H-C(14)); 2.22-2.10 (m, H-C(7), H'-C(7)); 1.89 (dd, J=5.6 Hz, 12.5 Hz, H-C(8)); 1.24 (d, J=7.5 Hz, Me-C(14)); 1.11 (s, t-Bu).

NMR $^{13}$C (100 MHz, CD$_3$OD): 178.1 (s); 175.2 (s); 173.1 (s); 110.8 (d); 103.2 (s); 94.2 (d); 85.8 (s); 81.1 (d); 80.3 (d); 74.9 (s); 74.7 (d); 74.2 (d); 73.3 (d); 71.0 (d); 70.6 (s); 70.4 (d); 61.9 (t); 50.8 (d); 42.8 (d); 37.8 (t); 33.4 (s); 29.6 (3q); 9.6 (q).

2.7. 10-O-(β-D-glucopyranosyl)ginkgolide B (21):

A mixture of 9 (32.0 mg, 0.034 mmol) as obtained for example in Stage 2.1. or 2.2., and 10% Pd/C (100 mg) in MeOH (3.0 ml) was hydrogenated for 17 hours under a pressure of 3.5 atm. After filtration, evaporation and flash chromatography (750 g silica, eluant AcOEt/MeOH/H$_2$O 8.5:1.5:1), 21 (19.8 mg, 88%) was obtained.

NMR $^1$H (500 MHz, acetone (D$_6$)): 6.15 (s, H-C(12)); 5.43 (d, J=4.0 Hz, H-C(6)); 5.27 (s, exchanged by D$_2$O, HO-C(3)); 3.87–3.83 (m, H-C(6')); 3.78 (m, H'-C(6')); 3.66–3.62 (m, H-C(5')); 3.49–3.45 (m, H-C(2')); 3.41–3.34 (m, H-C(3'), H-C(4')); 3.02 (q, J=7.1 Hz, H-C(14)); 2.28 (dd, J=4.3 Hz, 13.5 Hz, H-C(7)); 2.08–2.01 (m, H'-C(7)); 1.93 (dd, J=4.3 Hz, 14.6 Hz, H-C(8)); 1.26 (d, J=7.1 Hz, Me-C (14)); 1.21 (s, t-Bu).

NMR $^{13}$C (125 MHz, acetone (D$_6$)): 176.7 (s); 171.6 (s); 171.1 (s); 110.0 (d); 99.8 (s); 93.3 (d); 84.1 (s); 79.4 (d); 78.8 (d); 77.7 (d); 75.6 (d); 75.5 (d); 73.6 (s); 72.7 (d); 71.6 (d); 69.2 (s); 62.6 (t); 50.5 (d); 43.0 (d); 37.7 (t); 32.9 (s); 29.7 (3q); (8.2 (q).

2.8. 10-O-(α-D-glucopyranosyl)ginkgolide B (22):

A mixture of 10 (45.1 mg, 0.048 mmol) as obtained for example in Stage 2.1. or 2.2., and 10% Pd/C (50 mg) in MeOH (3.0 ml) was hydrogenated for 17 hours under a pressure of 2.1 atm. After filtration and evaporation, 22 (27.5 mg, 98%) was obtained.

NMR $^1$H (300 MHz, CD$_3$OD): 6.14 (s, H-C(12)); 5.44 (d, J=4.0 Hz, H-C(6)); 3.79–3.73 (m, H-C(5')); 3.67–3.44 (m, 5 H); 3.06 (q, J=7.2 Hz, H-C(14)); 2.23 (dd, J=4.4 Hz, 13.4 Hz, H-C(7)); 2.01 (ddd, J=4.1 Hz, 13.6 Hz, 14.3 Hz, H'-C(7)); 1.81 (dd, J=4.3 Hz, 14.3 Hz, H-C(8)); 1.21 (d, J=7.2 Hz, Me-C(14)); 1.12 (s, t-Bu).

NMR $^{13}$C (100 MHz, CD$_3$OD): 178.5 (s); 173.1 (s); 172.8 (s); 111.2 (d); 100.3 (s); 94.7 (d); 83.6 (s); 80.4 (d); 74.8 (d); 74.8 (d); 74.1 (d); 73.5 (d);

73.4 (s); 72.4 (d); 70.2 (d); 69.8 (s); 61.5 (t); 50.2 (d); 43.4 (d); 38.3 (t); 33.4 (s); 29.9 (3q); 8.1 (q).

2.9. 3-O-(β-D-glucopyranosyl)-10-O-(α-D-glucopyranosyl) ginkgolide B (23)

A mixture of 11 (36.1 mg, 0.025 mmol) as obtained for example in Stage 2.2. or 2.3., and 10% Pd/C (50 mg) in MeOH (3.0 ml) and acetone (1.5 ml) was hydrogenated for 21 hours under a pressure of 1.2 atm. After filtration and evaporation, 23 (18.3 mg, 99%) was obtained.

NMR $^1$H (300 MHz, CD$_3$OD): 6.17 (s, H-C(12)); 5.50 (d, J=4.1 Hz, H-C(6)); 3.78–3.15 (m, 12 H); 3.08 (q, J=6.8 Hz, H-C(14)); 2.24 (dd, J=4.4 Hz, 13.7 Hz, H-C(7)); 2.02 (ddd, J=4.0 Hz, 13.7 Hz, 14.0 Hz, H'-C(7)); 1.80 (dd, J=4.0Hz, 14.3 Hz, H-C(8)); 1.31 (d, J=6.8 Hz, Me-C(14)); 1.12 (s, t-Bu).

2.10. 3.10-O-(β-D-glucopyranosyl)ginkgolide B (24):

A mixture of 12 (37.9 mg, 0.026 mmol) as obtained for example in Stage 2.2., and 10% Pd/C (50 mg) in MeOH (3.0 ml) and acetone (1.0 ml) was hydrogenated for 21 hours under a pressure of 2.3 atm. After filtration and evaporation, 24 (18.3 mg, 95%) was obtained.

NMR $^1$H (300 MHz, CD$_3$OD): 6.15 (s, H-C(12)); 5.52 (d, J=4.0 Hz, H-C(6)); 3.88 (dd, J=1.6 Hz, 12.5 Hz, 1 H); 3.75 (dd, J=2.3 Hz, 12.5 Hz, 1 H); 3.67 (dd, J=5.8 Hz, 12.5 Hz, I H); 3.61 (dd, J=4.7 Hz, 12.2 Hz, 1 H); 3.43–3.14 (m, 8H); 3.02 (q, J=6.8 Hz, H-C(14)); 2.27 (dd, J=4.4 Hz, 13.4 Hz, H-C(7)); 2.03 (ddd, J=4.4 Hz, 14.0 Hz, 14.6 Hz, H'-C(7)); 1.89 (dd, J=4.0 Hz, 14.6 Hz, H-C(8)); 1.33 (d, J=6.8 Hz, Me-C(14)); 1.13 (s, t-Bu).

NMR $^{13}$C (100MHz, CD$_3$OD): 178.9 (s); 172.7 (s); 172.1 (s); 111.8 (d); 100.5 (s); 90.0 (s); 88.1 (d); 80.3 (d); 79.2 (d); 78.6 (d); 77.9 (d); 77.8 (d); 76.6 (d); 75.5 (d); 74.6 (d); 74.0 (s); 73.5 (d); 71.3 (d); 70.9 (d); 69.6 (s); 62.6 (t); 62.3 (t); 51.2 (d); 43.9 (d); 38.0 (t); 33.2 (s); 29.7 (3q); 8.3 (q).

2.11. 1.3-O-(β-D-glucopyranosyl)ginkgolide B (25)

A mixture of 14 (17.1 mg, 0.012 mmol) as obtained for example in Stage 2.2., and 10% Pd/C (50 mg) in MeOH (3.0 ml) and acetone (1.5 ml) was hydrogenated for 21 hours under a pressure of 1.2 atm. After filtration and evaporation, 25 (8.5 mg, 97%) was obtained.

NMR $^1$H (300 MHz, CD$_3$OD): 6.08 (s, H-C(12)); 5.58 (d, J=2.5 Hz, H-C(6)); 3.86 (dd, J=2.5 Hz, 12.1 Hz, 1 H); 3.78 (dd, J=2.2 Hz, 12.1 Hz, 1 H); 3.72 (dd J=5.0 Hz, 12.1 Hz, 1 H); 3.59 (dd, J=5.3 Hz, 12.1 Hz, 1 H); 3.41–3.18 (m, 8H); 3.11 (q, J=7.2 Hz, H-C(14)); 2.24–2.10 (m, H-C(7), H'-C (7)); 1.89 (dd, J=5.3 Hz, 13.1 Hz, H-C(8)); 1.32 (d, J=7.2 Hz, Me-C(14)); 1.12 (s, t-Bu).

NMR $^{13}$C (100 MHz, CD$_3$OD): 178.5 (s); 175.1 (s); 172.0 (s); 111.4 (d); 101.4 (s); 91.3 (s); 88.9 (d); 84.5 (d); 81.0 (d); 78.5 (d); 78.0 (d); 77.9 (d); 77.8 (d); 75.2 (d); 74.6 (d); 73.4 (s); 71.2 (d); 71.1 (d); 70.4 (s); 70.0 (d); 62.4 (t); 62.3 (t); 50.6 (d); 43.6 (d); 38.0 (t); 33.4 (s); 29.6 (3q); 9.2 (q).

2.12. 1.3.10-O-(β-D-glucopyranosyl)ginkgolide B (26)

A mixture of 16 (53.0 mg, 0.027 mmol) as obtained for example in stage 2.3., and 10% Pd/C (50 mg) in MeOH (3.0 ml) and acetone (1.5 ml) was hydrogenated for 21 hours under a pressure of 1.2 atm. After filtration and evaporation, 26 (23.5 mg, 97%) was obtained.

NMR $^1$H (300 MHz, CD$_3$OD): 6.05 (s, H-C(12)); 5.75 (d, J=3.4 Hz, H-C(6)); 3.90–3.16 (m, 18 H); 3.08 (q, J=7.5 Hz, H-C(14)); 2.30 (dt, J=4.1 Hz, 14.0 Hz, H-C(7)); 2.18-2.11 (m, H'-C(7)); 1.91 (dd, J=4.4 Hz, 14.3 Hz, H-C(8)); 1.32 (d, J=6.8 Hz, Me-C(14)); 1.14 (s, t-Bu).

NMR $^{13}$C (100 MHz, CD$_3$OD): 177.8 (s); 172.8 (s); 172.1 (s); 109.8 (d); 104.8 (s); 92.3 (s); 91.5 (d); 85.6 (d); 80.6 (d); 78.9 (d); 78.5 (d); 78.2 (d); 78.1 (d); 78.0 (d); 77.9 (d); 77.7 (d); 76.1 (s); 75.3 (d); 74.7 (d); 74.4 (d); 71.8 (d); 71.5 (d); 70.9 (d); 70.8 (s); 62.9 (t); 62.8 (t); 61.9 (t); 51.7 (d); 43.1 (d); 37.6 (t); 33.1 (s); 30.2 (3q); 11.9 (q).

Example 3

10-O-acetyl-3-O-[(4-O-β-D-galactopyranosyl)-β-D-glucopyranosyl]ginkgolide A (30)

3.1. 10O-acetyl-3-O-[2,3,6,-O-benzyl 4-O-(2,3,4,6-tetra-O-benzyl-β-D-galactopyranosyl)-β-D-glucopyranosyl] ginkgolide A (28)

Ginkgolide A (1) (7 mg, 15 μmol) was treated with a 1-azi-2,3,6-tri-O-benzyl-4-O-[2,3,4,6-tetra-O-benzyl-D-galactopyranosyl]1-deoxy-D-glucopyranose solution (27) (50 mg, 51 μmol; obtained according to methods similar to those mentioned for other glycosyl diazirines) in THF (1 ml), and agitated for 1 hour at 25° C. After evaporation and HPLC (eluant hexane/acetone 3:2), 28 (20 mg, 90%) was obtained.

NMR $^1$H (300 MHz, CDCl$_3$): 7.41–7.03 (m, 35 H); 6.10(s); 6.05 (s, H-C(10), H-C(12)); 5.16–5.08 (m, 2H); 4.95 (d, J=11.2 Hz, PhCH); 4.83–4.33 (m, 15 H); 4.25 (d, J=12.0 Hz, PhCH); 4.10 (t, J=9.1 Hz, 1 H); 3,90–3.34 (m, 10 H); 3.17–3.06 (m, 2H); 2.70 (dd, J=7.5 Hz, 14.9 Hz, H-C(1)); 2.21 (s, AcO); 2.15–1.73 (m, 4 H); 1.45 (d, J=6.6 Hz, Me-C(14)); 1.04 (s, t-Bu).

3.2. 10-O-acetyl-3-O-[4-O-(β-D-galactopyranosyl)-β-D-glucopyranosyl]ginkgolide A (29)

28 (20 mg, 14 μmol) in the presence of 10% Pd/C (100 mg) in MeOH (5 ml) was hydrogenated under a pressure of 3 atm for 17 hours. After filtration and evaporation, 29 (11 mg, 100%) was obtained.

NMR $^1$H (300 MHz, CD$_3$OD): 6.24 (s); 6.17 (d, H-C(10), H-C(12)); 5.53 (t, J=8.4 Hz, H-C(2)); 4.98 (d, J=3.7 Hz, H-C(6)); 4.53 (d, J=7.5 Hz, H-C(1')); 4.36 (d, J=7.2 Hz, H-C(1")); 3.81–3.24 (m, 12 H); 3.15 (q, J=6.8 Hz, H-C(14)); 3.03 (dd, J=7.8 Hz, 14.6 Hz, H-C(1)); 2.26–2.21 (m, 1 H); 2.21 (s, AcO); 2.09 (ddd, J=4.0 Hz, 13.7 Hz, 13.8 Hz, H-C(7)); 1.98–1.86 (m, 2H); 1.35 (d, J=6.8 Hz, Me-C(14)); 1.05 (s, t-Bu).

3.3. 3-O-[4-O-(β-D-galactopyranosyl)-β-D-glucopyranosyl]ginkgolide A (30)

30 is obtained by deacetylation of 29 using standard methods (treatment for example with ammonium hydroxide in methanol; cf. Stage 1.3.).

What is claimed is:

1. A compound of the formula

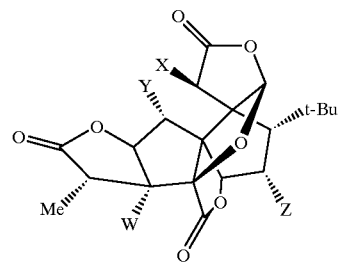

I wherein W, X, Y and Z are individually selected from the group consisting of hydrogen, —OH, alkoxy of 1 to 6 carbon atoms and —O—G$_s$ derived from G$_s$—OH wherein G$_s$—OH is a member of the group consisting of monosaccharide, disaccharide and derivatives thereof with the proviso that at least of W, X, Y and Z is —OG$_s$.

2. A compound of claim 1 wherein X is —OH or —OG$_s$ and W is —OH or OG$_s$ when Y and Z are hydrogen or W is —OH or —OG$_s$ when Y and Z are —OH or —OG$_s$ or W is —OH or —OG$_s$ when Y is hydrogen and Z is —OH or —OG$_s$ or W is hydrogen when Y and Z are —OH or —OG$_s$ or W is —OH or —G$_s$ when Y is alkoxy and Z is hydrogen, or W=—OH or —OG$_3$, Y is —OH or —OG$_3$ and Z is H with the proviso that at least one of W, X, Y and Z being —OG$_s$.

3. A compound of claim 1 wherein X is —OH or —OG$_s$ and W is —OH or —OG$_s$ when Y and Z are hydrogen or W is —OH or —OG$_s$ when Y is —OH or OG$_s$ and Z is hydrogen or W is —OH or —OG$_s$ when Y is alkoxy and Z is hydrogen with the proviso that at least one of W, X, Y and Z is —OG$_s$.

4. A compound of claim 1 wherein —OG$_s$ is selected from the group consisting of abequose, rhamnose, arabinose, ribose, xylose, 2-deoxyribose, glucose, galactose, mannose, 2-deoxyglucose, fructose, fucose, N-acetylglucosamine, N-acetylallosamine, galactosamine, mannosamine, saccharose, lactose, maltose, cellobiose and trehalose.

5. A compound of claim 1 wherein —$OG_s$ is glucose or lactose.

6. A composition for combatting vascular diseases comprising an amount of a compound of claim 1 sufficient to treat vascular disease and an inert pharmaceutical carrier.

7. A method of treating vascular diseases in warm-blooded animals comprising administering to warm-blooded animals an amount of a compound of claim 1 sufficient to treat vascular diseases.

8. A process for the preparation of a compound of claim 1 comprising reacting a compound of the formula

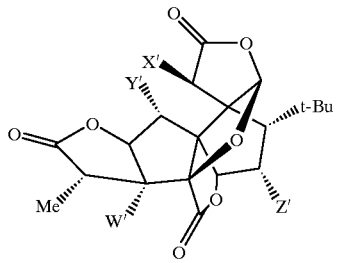

III wherein W', X', Y' and Z' are individually selected from the group consisting of hydrogen, —OH, alkoxy of 1 to 6 carbon atoms and —$OG_x$, $G_x$ being a hydroxy protective group capable of being removed in a neutral or basic medium with a glycosyl diazirine of the formula

II when $G_p$ is derived from a $G_p$—OH sugar, all hydroxyl groups except that on the anomeric carbon being protected wherein the hydroxyl on the anomeric position and the hydrogen attached to the same carbon atom are substituted with azi.

* * * * *